United States Patent [19]

Desai et al.

[11] Patent Number: 5,916,596
[45] Date of Patent: Jun. 29, 1999

[54] PROTEIN STABILIZED PHARMACOLOGICALLY ACTIVE AGENTS, METHODS FOR THE PREPARATION THEREOF AND METHODS FOR THE USE THEREOF

[75] Inventors: Neil P. Desai, Los Angeles; Chunlin Tao, Beverly Hills; Andrew Yang, Rosemead; Leslie Louie, Montebello; Tianli Zheng; Zhiwen Yao, both of Culver City; Patrick Soon-Shiong, Los Angeles, all of Calif.; Shlomo Magdassi, Jerusalem, Israel

[73] Assignee: Vivorx Pharmaceuticals, Inc., Santa Monica, Calif.

[21] Appl. No.: 08/720,756

[22] Filed: Oct. 1, 1996

Related U.S. Application Data

[60] Continuation-in-part of application No. 08/412,726, Mar. 29, 1995, Pat. No. 5,560,933, which is a division of application No. 08/023,698, Feb. 22, 1993, Pat. No. 5,439,686.

[51] Int. Cl.$^6$ ........................................... A61K 9/14
[52] U.S. Cl. .......................... 424/489; 424/450; 424/465; 424/451; 424/439
[58] Field of Search ...................................... 424/489, 422, 424/423, 475, 9.1, 9.3, 9.32, 450, 400

[56] References Cited

U.S. PATENT DOCUMENTS

| | | |
|---|---|---|
| 3,959,457 | 5/1976 | Speaker et al. . |
| 4,073,943 | 2/1978 | Wretlind et al. . |
| 4,247,406 | 1/1981 | Widder et al. . |
| 4,572,203 | 2/1986 | Feinstein . |

(List continued on next page.)

FOREIGN PATENT DOCUMENTS 0 129 619 A1  1/1985  European Pat. Off. .
0 295 941 A2  12/1988  European Pat. Off. .
0 391 518 A2  2/1990  European Pat. Off.

(List continued on next page.)

OTHER PUBLICATIONS

Burgess et al., "Potential use of albumin microspheres as a drug delivery system. I. Preparation and in vitro release of steroids," *International Journal of Pharmaceutics*, 39:129–136 (1987).

(List continued on next page.)

*Primary Examiner*—Neil S. Levy
*Assistant Examiner*—William E. Benston, Jr.
*Attorney, Agent, or Firm*—Gray, Cary, Ware & Freidenrich; Stephen E. Reiter

[57] ABSTRACT

In accordance with the present invention, there are provided compositions and methods useful for the in vivo delivery of substantially water insoluble pharmacologically active agents (such as the anticancer drug paclitaxel) in which the pharmacologically active agent is delivered in the form of suspended particles coated with protein (which acts as a stabilizing agent). In particular, protein and pharmacologically active agent in a biocompatible dispersing medium are subjected to high shear, in the absence of any conventional surfactants, and also in the absence of any polymeric core material for the particles. The procedure yields particles with a diameter of less than about 1 micron. The use of specific composition and preparation conditions (e.g., addition of a polar solvent to the organic phase), and careful selection of the proper organic phase and phase fraction, enables the reproducible production of unusually small nanoparticles of less than 200 nm diameter, which can be sterile-filtered. The particulate system produced according to the invention can be converted into a redispersible dry powder comprising nanoparticles of water-insoluble drug coated with a protein, and free protein to which molecules of the pharmacological agent are bound. This results in a unique delivery system, in which part of the pharmacologically active agent is readily bioavailable (in the form of molecules bound to the protein), and part of the agent is present within particles without any polymeric matrix therein.

31 Claims, 2 Drawing Sheets

U.S. PATENT DOCUMENTS

| | | |
|---|---|---|
| 4,671,954 | 6/1987 | Goldberg et al. . |
| 4,718,433 | 1/1988 | Feinstein . |
| 4,789,550 | 12/1988 | Hommel et al. . |
| 4,844,882 | 7/1989 | Widder et al. . |
| 5,059,699 | 10/1991 | Kingston et al. ............. 549/511 |
| 5,110,606 | 5/1992 | Geyer et al. . |
| 5,145,684 | 9/1992 | Liversidge et al. ............. 424/489 |
| 5,362,478 | 11/1994 | Desai et al. ............................ 424/9 |
| 5,439,686 | 8/1995 | Desai et al. ............................ 424/451 |
| 5,498,421 | 3/1996 | Grinstaff et al. ............. 424/450 |
| 5,505,932 | 4/1996 | Gristaff et al. ............. 424/9.3 |
| 5,508,021 | 4/1996 | Grinstaff et al. ............. 424/9.322 |
| 5,512,268 | 4/1996 | Grinstaff et al. ............. 424/9.322 |
| 5,560,933 | 10/1996 | Soon-Shing et al. ............. 424/489 |
| 5,650,156 | 7/1997 | Grinstaff et al. ............. 424/400 |
| 5,665,382 | 9/1997 | Grinstaff et al. ............. 424/450 |

FOREIGN PATENT DOCUMENTS

| | | |
|---|---|---|
| 0 361 677 A1 | 4/1990 | European Pat. Off. . |
| 0 418 153 A1 | 3/1991 | European Pat. Off. . |
| 0 190 050 B1 | 5/1991 | European Pat. Off. . |
| 0 213 303 B1 | 9/1991 | European Pat. Off. . |
| 2660556 | 10/1991 | France . |
| WO 85/00011 | 1/1985 | WIPO . |
| WO 87/01035 | 2/1988 | WIPO . |
| WO 88/01506 | 3/1988 | WIPO . |
| WO 88/07365 | 10/1988 | WIPO . |
| WO 89/03674 | 5/1989 | WIPO . |
| WO 90/13285 | 11/1990 | WIPO . |
| WO 90/13780 | 11/1990 | WIPO . |
| WO 91/15947 | 10/1991 | WIPO . |
| WO 94/10980 | 5/1994 | WIPO . |

OTHER PUBLICATIONS

Chen et al., "Comparison of albumin and casein microspheres as a carrier for doxorubicin," *J. Pharm. Pharmacol.,* 39:978–985 (1987).

Feinstein et al., "Two–Dimensional Constrast Echocardiography. I. In Vitro Development and Quantitative Analysis of Echo Contrast Agents," *JACC,* 3(1):14–20 (1984).

Grinstaff & Suslick, "Nonaqueous Liquid Filled Microcapsules," *Polym. Prepr.,* 32:255–256 (1991).

Gupta et al., "Albumin microspheres. III. Synthesis and characterization of microspheres containing adriamycin and magnetite," *International Journal of Pharmaceutics,* 43:167–177 (1988).

Ishizaka et al., "Preparation of Egg Albumin Microcapsules and Microspheres," *Journal of Pharmaceutical Sciences,* 70(4):358–363 (1981).

Klibanov et al., "Amphipathic polyethyleneglycols effectively prolong the circulation time of liposomes," *FEBS,* 268(1):235–237 (1990).

Koenig & Meltzer, "Effect of Viscosity on the Size of Microbubbles Generated for Use as Echocardiographic Contrast Agents," *Journal of Cardiovascular ultrasonography,* 5(1):3–4 (1986).

Molecular Biosystems, Inc., "ALBUNEX—Preclinical Investigator's Package".

Moseley et al., "Microbubbles: A Novel MR Susceptibility Contrast Agent," 10th Annual Meeting of Society of Magnetic Resonance in Medicine (1991).

Suslick & Grinstaff, "Protein Microencapsulation of Nonaqueous Liquids," *J. Am. Chem. Soc.,* 112(21):7807–7809 (1990).

Willmott & Harrison, "Characterisation of freeze–dried albumin microspheres containing the anti–cancer drug adriamycin," *International Journal of Pharmaceutics,* 43:161–166 (1988).

———, "Serum Albumin Beads: An Injectable, Biodegradable System for the Sustained Release of Drugs," *Science,* 213(10):233–235 (1981).

Bazile et. al., "Body distribution of fully biodegeradable [$^{14}$C]–poly(latic acid) nanoparticles coated with albumin after parenteral adminstration to rats" *Biomaterials,* 13:1093–1102 (1992).

Boury et al., "Dilatational Properties of Absorbed Poly(D, L–lactide) and Bovine Serum Albumin Monolayers at the Dichloromethane/Water Interface" *Langmuir,* 11:1636–1644 (1995).

Calvo et al., "Comparative in Vitro Evaluation of Several Colloidal Systems, Nanoparticles, Nanocapsules, and Nanoemulsions, as Ocular Drug Carriers" *J. Pharm. Sci.,* 85(5):530–536 (1996).

Cavalier et al., "The formation and characterization of hydrocortisone–loaded poly((+_)–lactide) microspheres" *J. Pharm. Pharmacol.,* 38:249–253 (1985).

Kumar et al., "Binding of Taxol to Human Plasma, Albumin and—Acid Glycoprotein" *Research Communications in Chemical Pathology and Pharmacology,* 80(3):337–344 (1993).

Lee et al., "Serum Albumin Beads: An Injectable, Biodegradable System for the Sustained Release of Drugs" *Science,* 213:233–235 (1981).

Leucuta et al., "Albumin microspheres as a drug delivery system for epirubicin: pharmaceutical, pharmacokinetic and biological aspects" *International Journal of Pharmaceutics,* 41:213–217 (1988).

Liversideg–Merisko et al., "Formulation and Antitumor Activity Evaluation of Nanocrystalline Suspensions of Poorly Soluble Anticacer Drugs" *Pharmaceutical Research,* 13(2):272–278 (1996).

Mathew et al., "Synthesis and Evaluation of Some Water–Soluble Prodrugs and Derivatives of Taxol with Antitumor Activity" *J. Med. Chem.,* 35:145–151 (1992).

Norton et al., *Abstracts of the 2nd National Cancer Institute Workshop on Taxol & Taxus,* Sep. 23–24, 1992).

Wani et al., "Plant Antitumor Agents. VI. The Isolation and Structure of Toxol, a Novel Antileukemic and Antitumor Agents from *Taxus brevifolia*[1,2]" *J. Am. Chem. Soc.,* 93:2325–2327 (1971).

PROTEIN STABILIZED PHARMACOLOGICALLY ACTIVE AGENTS, METHODS FOR THE PREPARATION THEREOF AND METHODS FOR THE USE THEREOF

RELATED APPLICATIONS

This application is a continuation-in-part of U.S. Ser. No. 08/412,726, filed Mar. 29, 1995, now issued as U.S. Pat. No. 5,560,933, which is, in turn, a divisional of U.S. Ser. No. 08/023,698, filed Feb. 22, 1993, now issued as U.S. Pat. No. 5,439,686, the entire contents of both of which are hereby incorporated by reference herein in their entirety.

FIELD OF THE INVENTION

The present invention relates to methods for the production of particulate vehicles for the intravenous administration of pharmacologically active agents, as well as novel compositions produced thereby. In a particular aspect, the invention relates to methods for the in vivo delivery of substantially water insoluble pharmacologically active agents (e.g., the anticancer drug taxol). In another aspect, dispersible colloidal systems containing water insoluble pharmacologically active agents are provided. The suspended particles are encased in a polymeric shell formulated from a biocompatible polymer, and have a diameter of less than about 1 micron. Invention colloidal systems are prepared without the use of conventional surfactant or any polymeric core matrix. In a presently preferred aspect of the invention, there is provided a method for preparation of extremely small particles which can be sterile-filtered. The polymeric shell contains particles of pharmacologically active agent, and optionally a biocompatible dispersing agent in which pharmacologically active agent can be either dissolved or suspended. Thus, the invention provides a drug delivery system in either liquid form or in the from of a redispersible powder. Either form provides both immediately bioavailable drug molecules (i.e., drug molecules which are molecularly bound to a protein), and pure drug particles coated with a protein.

BACKGROUND OF THE INVENTION

Intravenous drug delivery permits rapid and direct equilibration with the blood stream which carries the medication to the rest of the body. To avoid the peak serum levels which are achieved within a short time after intravascular injection, administration of drugs carried within stable carriers would allow gradual release of the drugs inside the intravascular compartment following a bolus intravenous injection of the therapeutic nanoparticles.

Injectable controlled-release nanoparticles can provide a pre-programmed duration of action, ranging from days to weeks to months from a single injection. They also can offer several profound advantages over conventionally administered medicaments, including automatic assured patient compliance with the dose regimen, as well as drug targeting to specific tissues or organs (Tice and Gilley, *Journal of Controlled Release* 2:343–352 (1985)).

Microparticles and foreign bodies present in the blood are generally cleared from the circulation by the "blood filtering organs", namely the spleen, lungs and liver. The particulate matter contained in normal whole blood comprises red blood cells (typically 8 microns in diameter), white blood cells (typically 6–8 microns in diameter), and platelets (typically 1–3 microns in diameter). The microcirculation in most organs and tissues allows the free passage of these blood cells. When microthrombii (blood clots) of size greater than 10–15 microns are present in circulation, a risk of infarction or blockage of the capillaries results, leading to ischemia or oxygen deprivation and possible tissue death. Injection into the circulation of particles greater than 10–15 microns in diameter, therefore, must be avoided. A suspension of particles less than 7–8 microns, is however, relatively safe and has been used for the delivery of pharmacologically active agents in the form of liposomes and emulsions, nutritional agents, and contrast media for imaging applications.

The size of particles and their mode of delivery determines their biological behavior. Strand et al. (in *Microspheres-Biomedical Applications*, ed. A. Rembaum, pp 193–227, CRC Press (1988)) have described the fate of particles to be dependent on their size. Particles in the size range of a few nanometers (nm) to 100 nm enter the lymphatic capillaries following interstitial injection, and phagocytosis may occur within the lymph nodes. After intravenous/intraarterial injection, particles less than about 2 microns will be rapidly cleared from the blood stream by the reticuloendothelial system (RES), also known as the mononuclear phagocyte system (MPS). Particles larger than about 7 microns will, after intravenous injection, be trapped in the lung capillaries. After intraarterial injection, particles are trapped in the first capillary bed reached. Inhaled particles are trapped by the alveolar macrophages.

Pharmaceuticals that are water-insoluble or poorly water-soluble and sensitive to acid environments in the stomach cannot be conventionally administered (e.g., by intravenous injection or oral administration). The parenteral administration of such pharmaceuticals has been achieved by emulsification of the oil solubilized drug with an aqueous liquid (such as normal saline) in the presence of surfactants or emulsion stabilizers to produce stable microemulsions. These emulsions may be injected intravenously, provided the components of the emulsion are pharmacologically inert. U.S. Pat. No. 4,073,943 describes the administration of water-insoluble pharmacologically active agents dissolved in oils and emulsified with water in the presence of surfactants such as egg phosphatides, pluronics (copolymers of polypropylene glycol and polyethylene glycol), polyglycerol oleate, etc. PCT International Publication No. WO85/00011 describes pharmaceutical microdroplets of an anaesthetic coated with a phospholipid such as dimyristoyl phosphatidylcholine having suitable dimensions for intradermal or intravenous injection.

An example of a water-insoluble drug is taxol, a natural product first isolated from the Pacific Yew tree, *Taxus brevifolia*, by Wani et al. (*J. Am. Chem. Soc.* 93:2325 (1971)). Among the antimitotic agents, taxol, which contains a diterpene carbon skeleton, exhibits a unique mode of action on microtubule proteins responsible for the formation of the mitotic spindle. In contrast with other antimitotic agents such as vinblastine or colchicine, which prevent the assembly of tubulin, taxol is the only plant product known to inhibit the depolymerization process of tubulin, thus preventing the cell replication process.

Taxol, a naturally occurring diterpenoid, has been shown to have significant antineoplastic and anticancer effects in drug-refractory ovarian cancer. Taxol has shown excellent antitumor activity in a wide variety of tumor models such as the B16 melanoma, L1210 leukemias, MX-1 mammary tumors, and CS-1 colon tumor xenografts. Several recent press releases have termed taxol as the new anticancer wonder-drug. Indeed, taxol has recently been approved by the Federal Drug Administration for treatment of ovarian cancer. The poor aqueous solubility of taxol, however, presents a problem for human administration. Indeed, the delivery of drugs that are inherently insoluble or poorly soluble in an aqueous medium can be seriously impaired if oral delivery is not effective. Accordingly, currently used taxol formulations require a cremaphor to solubilize the drug. The human clinical dose range is 200–500 mg. This dose is dissolved in a 1:1 solution of ethanol:cremaphor and diluted to one liter of fluid given intravenously. The cremaphor currently used is polyethoxylated castor oil.

In phase I clinical trials, taxol itself did not show excessive toxic effects, but severe allergic reactions were caused by the emulsifiers employed to solubilize the drug. The current regimen of administration involves treatment of the patient with antihistamines and steroids prior to injection of the drug to reduce the allergic side effects of the cremaphore.

In an effort to improve the water solubility of taxol, several investigators have modified its chemical structure with functional groups that impart enhanced water-solubility. Among them are the sulfonated derivatives (Kingston et al., U.S. Pat. No. 5,059,699 (1991)), and amino acid esters (Mathew et al., J. Med. Chem. 35:145–151 (1992)) which show significant biological activity. Modifications to produce a water-soluble derivative facilitate the intravenous delivery of taxol dissolved in an innocuous carrier such as normal saline. Such modifications, however, add to the cost of drug preparation, may induce undesired side-reactions and/or allergic reactions, and/or may decrease the efficiency of the drug.

Protein microspheres have been reported in the literature as carriers of pharmacological or diagnostic agents. Microspheres of albumin have been prepared by either heat denaturation or chemical crosslinking. Heat denatured microspheres are produced from an emulsified mixture (e.g., albumin, the agent to be incorporated, and a suitable oil) at temperatures between 100° C. and 150° C. The microspheres are then washed with a suitable solvent and stored. Leucuta et al. (*International Journal of Pharmaceutics* 41:213–217 (1988)) describe the method of preparation of heat denatured microspheres.

The procedure for preparing chemically crosslinked microspheres involves treating the emulsion with glutaraldehyde to crosslink the protein, followed by washing and storage. Lee et al. (*Science* 213:233–235 (1981)) and U.S. Pat. No. 4,671,954 teach this method of preparation.

The above techniques for the preparation of protein microspheres as carriers of pharmacologically active agents, although suitable for the delivery of water-soluble agents, are incapable of entrapping water-insoluble ones. This limitation is inherent in the technique of preparation which relies on crosslinking or heat denaturation of the protein component in the aqueous phase of a water-in-oil emulsion. Any aqueous-soluble agent dissolved in the protein-containing aqueous phase may be entrapped within the resultant crosslinked or heat-denatured protein matrix, but a poorly aqueous-soluble or oil-soluble agent cannot be incorporated into a protein matrix formed by these techniques.

One conventional method for manufacturing drug-containing nanoparticles comprises dissolving polylactic acid (or other biocompatible, water insoluble polymers) in a water-immiscible solvent (such as methylene chloride or other chlorinated, aliphatic, or aromatic solvent), dissolving the pharmaceutically active agent in the polymer solution, adding a surfactant to the oil phase or the aqueous phase, forming an oil-in-water emulsion by suitable means, and evaporating the emulsion slowly under vacuum. If the oil droplets are sufficiently small and stable during evaporation, a suspension of the polymer in water is obtained. Since the drug is initially present in the polymer solution, it is possible to obtain by this method, a composition in which the drug molecules are entrapped within particles composed of a polymeric matrix. The formation of microspheres and nanoparticles by using the solvent evaporation method has been reported by several researchers (see, for example, Tice and Gilley, in *Journal of Controlled Release* 2:343–352 (1985); Bodmeier and McGinity, in *Int. J. Pharmaceutics* 43:179 (1988); Cavalier et al., in *J. Pharm. Pharmacol.* 38:249 (1985); and D'Souza et al., WO 94/10980) while using various drugs.

Bazile et. al., in *Biomaterials* 13:1093 (1992), and Spenlehauer et al., in Fr Patent 2 660 556, have reported the formation of nanoparticles by using two biocompatible polymers, one (e.g. Polylactide) is dissolved in the organic phase, together with an active component such as a drug, and the other polymer, such as albumin is used as the surface active agent. After emulsification and removal of the solvent, nanoparticles are formed, in which the drug is present inside the polymeric matrix of the polylactide particles.

The properties of the polymer solution from which the polymeric matrix is formed are very important to obtain the proper emulsion in the first stage. For example, polylactide (the polymer commonly used in the preparation of injectable nanoparticles), has a surface activity which causes the rapid adsorption thereof at the dichloromethane-water interface, causing reduced interfacial tension (see, for example, Boury et al., in *Langmuir* 11:1636 (1995)), which in turn improves the emulsification process. In addition, the same researchers found that Bovine Serum Albumin (BSA) interacts with the polylactide, and penetrates into the polylactide monolayer present at the oil-water interface. Therefore, it is expected, based on the above reference, that emulsification during the conventional solvent evaporation method is greatly favored by the presence of the surface active polymer (polylactide) in the nonaqueous organic phase. In fact, the presence of polylactide is not only a sufficient condition, but it is actually necessary for the formation of nanoparticles of suitable size.

Another process which is based on the solvent evaporation method comprises dissolving the drug in a hydrophobic solvent (e.g., toluene or cyclohexane), without any polymer dissolved in the organic solvent, adding a conventional surfactant to the mixture as an emulsifier, forming an oil-in-water emulsion, and then evaporating the solvent to obtain dry particles of the drug (see, for example, Sjostrom et al., in *J. Dispersion Science and Technology* 15:89–117 (1994)). Upon removal of the nonpolar solvent, precipitation of the drug inside the solvent droplets occurs, and submicron particles are obtained.

It has been found that the size of the particles is mainly controlled by the initial size of the emulsion droplets. In addition, it is interesting to note that the final particle size is reported to decrease with a decrease in the drug concentration in the organic phase. This finding is contrary to the results reported herein, wherein no conventional surfactant is used for the preparation of nanoparticles. In addition, it is noted by the authors of the Sjostrom paper that the drug used, cholesteryl acetate, is surface active in toluene, and hence may be oriented at the oil-water interface; therefore the concentration of drug at the interface is higher, thus increasing the potential for precipitation.

Formation of submicron particles has also been achieved by a precipitation process, as described by Calvo et al. in *J.*

*Pharm. Sci.* 85:530 (1996). The process is based on dissolving the drug (e.g., indomethacin) and the polymer (polycaprolactone) in methylene chloride and acetone, and then pouring the solution into an aqueous phase containing a surfactant (Poloxamer 188), to yield submicron size particles (216 nm). However, the process is performed at solvent concentrations at which no emulsion is formed.

BRIEF DESCRIPTION OF THE INVENTION

Thus it is an object of this invention to deliver pharmacologically active agents (e.g., taxol, taxane, Taxotere, and the like) in unmodified form in a composition that does not cause allergic reactions due to the presence of added emulsifiers and solubilizing agents, as are currently employed in drug delivery.

It is a further object of the present invention to deliver pharmacologically active agents in a composition of microparticles or nanoparticles, optionally suspended in a suitable biocompatible liquid.

It is yet another object of the present invention to provide a method for the formation of submicron particles (nanoparticles) of pharmacologically active agents by a solvent evaporation technique from an oil-in-water emulsion using proteins as stabilizing agents in the absence of any conventional surfactants, and in the absence of any polymeric core material.

These and other objects of the invention will become apparent upon review of the specification and claims.

In accordance with the present invention, we have discovered that substantially water insoluble pharmacologically active agents can be delivered in the form of microparticles or nanoparticles that are suitable for parenteral administration in aqueous suspension. This mode of delivery obviates the necessity for administration of substantially water insoluble pharmacologically active agents (e.g., taxol) in an emulsion containing, for example, ethanol and polyethoxylated castor oil, diluted in normal saline (see, for example, Norton et al., in *Abstracts of the 2nd National Cancer Institute Workshop on Taxol & Taxus*, Sep. 23–24, 1992). A disadvantage of such known compositions is their propensity to produce allergic side effects.

Thus, in accordance with the present invention, there are provided methods for the formation of nanoparticles of pharmacologically active agents by a solvent evaporation technique from an oil-in-water emulsion prepared under conditions of high shear forces (e.g., sonication, high pressure homogenization, or the like) without the use of any conventional surfactants, and without the use of any polymeric core material to form the matrix of the nanoparticle. Instead, proteins (e.g., human serum albumin) are employed as a stabilizing agent.

The invention further provides a method for the reproducible formation of unusually small nanoparticles (less than 200 nm diameter), which can be sterile-filtered through a 0.22 micron filter. This is achieved by addition of a water soluble solvent (e.g. ethanol) to the organic phase and by carefully selecting the type of organic phase, the phase fraction and the drug concentration in the organic phase. The ability to form nanoparticles of a size that is filterable by 0.22 micron filters is of great importance and significance, since formulations which contain a significant amount of any protein (e.g., albumin), cannot be sterilized by conventional methods such as autoclaving, due to the heat coagulation of the protein.

In accordance with another embodiment of the present invention, we have developed compositions useful for in vivo delivery of substantially water insoluble pharmacologically active agents. Invention compositions comprise substantially water insoluble pharmacologically active agents (as a solid or liquid) contained within a polymeric shell. The polymeric shell is a crosslinked biocompatible polymer. The polymeric shell, containing substantially water insoluble pharmacologically active agents therein, can then be suspended in a biocompatible aqueous liquid for administration.

The invention further provides a drug delivery system in which part of the molecules of pharmacologically active agent are bound to the protein (e.g., human serum albumin), and are therefore immediately bioavailable upon administration to a mammal. The other portion of the pharmacologically active agent is contained within nanoparticles coated by protein. The nanoparticles containing the pharmacologically active agent are present as a pure active component, without dilution by any polymeric matrix.

A large number of conventional pharmacologically active agents circulate in the blood stream bound to carrier proteins (through hydrophobic or ionic interactions) of which the most common example is serum albumin. Invention methods and compositions produced thereby provide for a pharmacologically active agent that is "pre-bound" to a protein (through hydrophobic or ionic interactions) prior to administration.

The present disclosure demonstrates both of the above-described modes of bioavailability for Taxol (Paclitaxel), an anticancer drug capable of binding to human serum albumin (see, for example, Kumar et al., in *Research Communications in Chemical Pathology and Pharmacology* 80:337 (1993)). The high concentration of albumin in invention particles, compared to Taxol, provides a significant amount of the drug in the form of molecules bound to albumin, which is also the natural carrier of the drug in the blood stream.

In addition, advantage is taken of the capability of human serum albumin to bind Taxol, as well as other drugs, which enhances the capability of Taxol to absorb on the surface of the particles. Since albumin is present on the colloidal drug particles (formed upon removal of the organic solvent), formation of a colloidal dispersion which is stable for prolonged periods is facilitated, due to a combination of electrical repulsion and steric stabilization.

In accordance with the present invention, there are also provided submicron particles in powder form, which can easily be reconstituted in water or saline. The powder is obtained after removal of water by lyophilization. Human serum albumin serves as the structural component of invention nanoparticles, and also as a cryoprotectant and reconstitution aid. The preparation of particles filterable through a 0.22 micron filter according to the invention method as described herein, followed by drying or lyophilization, produces a sterile solid formulation useful for intravenous injection.

The invention provides, in a particular aspect, a composition of anti-cancer drugs, e.g., Taxol, in the form of nanoparticles in a liquid dispersion or as a solid which can be easily reconstituted for administration. Due to specific properties of certain drugs, e.g., Taxol, such compositions can not be obtained by conventional solvent evaporation methods that rely on the use of surfactants. In the presence of various surfactants, very large drug crystals (e.g., size of about 5 microns to several hundred microns) are formed within a few minutes of storage, after the preparation process. The size of such crystals is typically much greater than the allowed size for intravenous injection.

While it is recognized that particles produced according to the invention can be either crystalline, amorphous, or a mixture thereof, it is generally preferred that the drug be present in the formulation in an amorphous form. This would lead to greater ease of dissolution and absorption, resulting in better bioavailability.

DETAILED DESCRIPTION OF THE INVENTION

Figure 1:
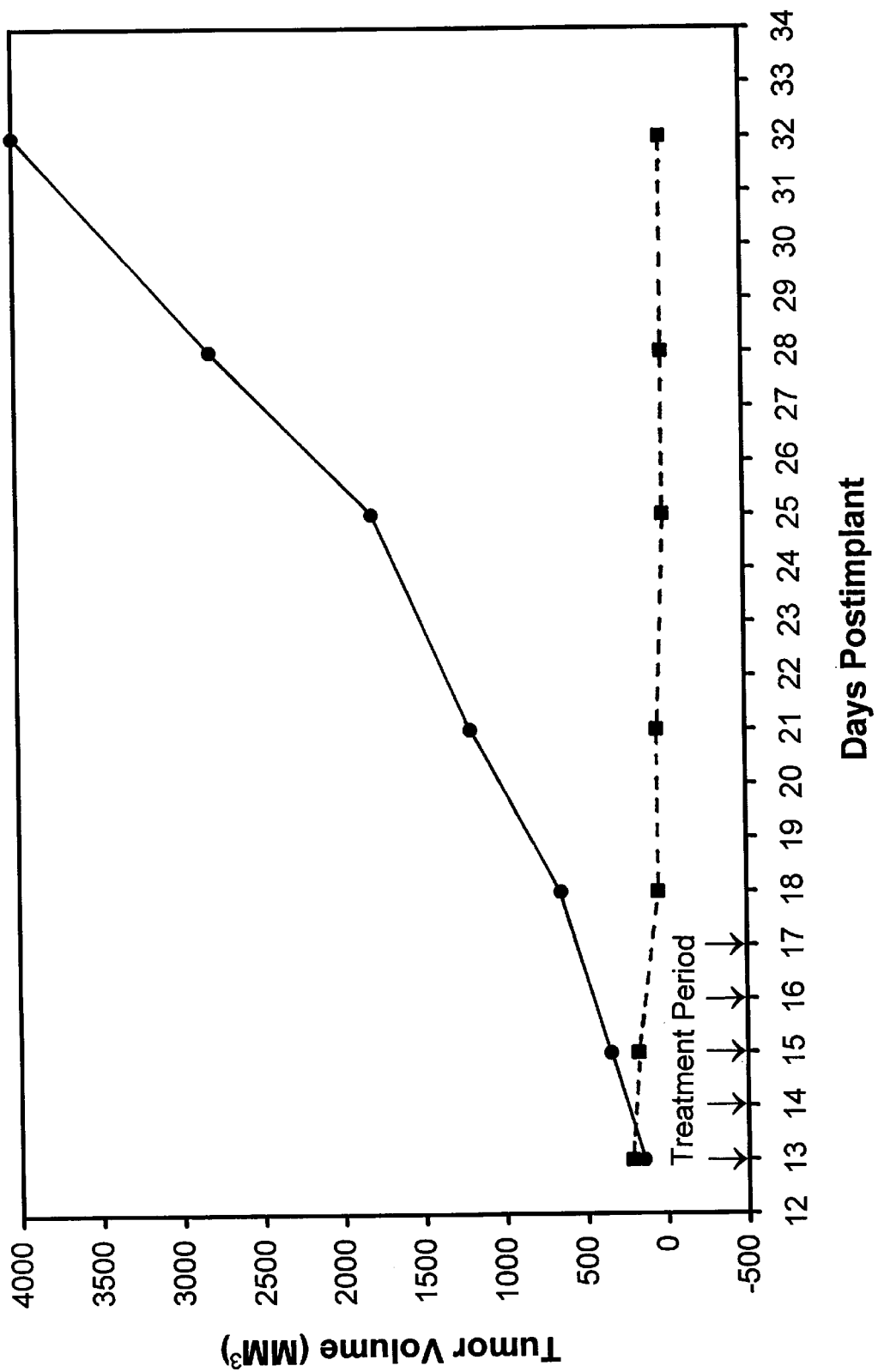
FIG. 1 presents the results of intravenous administration of paclitaxel nanoparticles to tumor bearing mice (n=5 in each group), showing a complete regression of tumor in the treatment group (■) compared with a control group receiving saline (●). Virtually uncontrolled tumor growth is seen in the control group. Dose for the treatment group is 20 mg/kg of paclitaxel administered as an intravenous bolus for five consecutive days.

In accordance with the present invention, there are provided methods for the preparation of substantially water insoluble pharmacologically active agents for in vivo delivery, said method comprising:
subjecting a mixture comprising:
an organic phase containing said pharmacologically active agent dispersed therein, and
aqueous medium containing biocompatible polymer, wherein said mixture contains substantially no surfactants,
in a high pressure homogenizer at a pressure in the range of about 3,000 up to 30,000 psi. Optionally, the organic and/or aqueous phases are thereafter removed from the mixture after having been subjected to high shear conditions.

Also provided in accordance with the present invention are compositions prepared by the above-described method.

In accordance with a still further embodiment of the present invention, there is provided a drug delivery system comprising particles of a solid or liquid, substantially water insoluble pharmacologically active agent, coated with a protein,
wherein said protein coating has free protein associated therewith,
wherein a portion of said pharmacologically active agent is contained within said protein coating and a portion of said pharmacologically active agent is associated with said free protein, and
wherein the average diameter of said particles is no greater than about 1 micron.

The above-described compositions are particularly advantageous as they have been observed to provide a very low toxicity form of a variety of pharmacologically active agents, e.g., the combination of taxol and albumin (as the biocompatible polymer) is a presently preferred combination because of its low toxicity. The combination of taxol and albumin also has the added advantage of being substantially non-myelosuppressive.

In a preferred embodiment, the average diameter of the above-described particles is no greater than about 200 nm. Such particles are particularly advantageous as they can be subjected to sterile filtration, thereby obviating the need for more vigorous treatment to achieve sterilization of solutions containing the desired pharmacologically active agent.

As used herein, the term "in vivo delivery" refers to delivery of a pharmacologically active agent by such routes of administration as oral, intravenous, subcutaneous, intraperitoneal, intrathecal, intramuscular, inhalational, topical, transdermal, suppository (rectal), pessary (vaginal), and the like.

As used herein, the term "micron" refers to a unit of measure of one one-thousandth of a millimeter.

As used herein, the term "biocompatible" describes a substance that does not appreciably alter or affect in any adverse way, the biological system into which it is introduced.

Key differences between the pharmacologically active agents contained in a polymeric shell according to the invention and protein microspheres of the prior art are in the nature of formation and the final state of the protein after formation of the particle, and its ability to carry poorly aqueous-soluble or substantially aqueous-insoluble agents. In accordance with the present invention, the polymer (e.g., a protein) may be crosslinked as a result of exposure to high shear conditions in a high pressure homogenizer. High shear is used to disperse a dispersing agent containing dissolved or suspended pharmacologically active agent into an aqueous solution of a biocompatible polymer, optionally bearing sulfhydryl or disulfide groups (e.g., albumin) whereby a shell of crosslinked polymer is formed around fine droplets of non-aqueous medium. The high shear conditions produce cavitation in the liquid that causes tremendous local heating and results in the formation of superoxide ions that are capable of crosslinking the polymer, for example, by oxidizing the sulfhydryl residues (and/or disrupting existing disulfide bonds) to form new, crosslinking disulfide bonds.

In contrast to the invention process, the prior art method of glutaraldehyde crosslinking is nonspecific and essentially reactive with any nucleophilic group present in the protein structure (e.g., amines and hydroxyls). Heat denaturation as taught by the prior art significantly and irreversibly alters protein structure. In contrast, disulfide formation contemplated by the present invention does not substantially denature the protein. In addition, particles of substantially water insoluble pharmacologically active agents contained within a shell differ from crosslinked or heat denatured protein microspheres of the prior art because the polymeric shell produced by the invention process is relatively thin compared to the diameter of the coated particle. It has been determined (by transmission electron microscopy) that the "shell thickness" of the polymeric coat is approximately 25 nanometers for a coated particle having a diameter of 1 micron (1000 nanometers). In contrast, microspheres of the prior art do not have protein shells, but rather, have protein dispersed throughout the volume of the microsphere.

Thus, in accordance with the present invention, a pharmacologically active agent is dissolved in a suitable solvent (e.g., chloroform, methylene chloride, ethyl acetate, ethanol, tetrahydrofuran, dioxane, acetonitrile, acetone, dimethyl sulfoxide, dimethyl formamide, methyl pyrrolidinone, or the like, as well as mixtures of any two or more thereof). Additional solvents contemplated for use in the practice of the present invention include soybean oil, coconut oil, olive oil, safflower oil, cotton seed oil, sesame oil, orange oil, limonene oil, C1–C20 alcohols, C2–C20 esters, C3–C20 ketones, polyethylene glycols, aliphatic hydrocarbons, aromatic hydrocarbons, halogenated hydrocarbons and combinations thereof.

Unlike conventional methods for nanoparticle formation, a polymer (e.g. polylactic acid) is not dissolved in the solvent. The oil phase employed in the preparation of invention compositions contains only the pharmacologically active agent dissolved in solvent.

Next, a protein (e.g., human serum albumin) is added (into the aqueous phase) to act as a stabilizing agent for the formation of stable nanodroplets. Protein is added at a concentration in the range of about 0.05 to 25 % (w/v), more preferably in the range of about 0.5%–5% (w/v). Unlike conventional methods for nanoparticle formation, no surfactant (e.g. sodium lauryl sulfate, lecithin, tween 80, pluronic F-68 and the like) is added to the mixture.

Next, an emulsion is formed by homogenization under high pressure and high shear forces. Such homogenization is conveniently carried out in a high pressure homogenizer, typically operated at pressures in the range of about 3,000 up to 30,000 psi. Preferably, such processes are carried out at pressures in the range of about 6,000 up to 25,000 psi. The resulting emulsion comprises very small nanodroplets of the nonaqueous solvent (containing the dissolved pharmacologically active agent) and very small nanodroplets of the protein stabilizing agent. Acceptable methods of homogenization include processes imparting high shear and cavitation such as high pressure homogenization, high shear mixers, sonication, high shear impellers, and the like.

Finally, the solvent is evaporated under reduced pressure to yield a colloidal system composed of protein coated nanoparticles of pharmacologically active agent and protein. Acceptable methods of evaporation include the use of rotary evaporators, falling film evaporators, spray driers, freeze driers, and the like.

Following evaporation of solvent, the liquid suspension may be dried to obtain a powder containing the pharmacologically active agent and protein. The resulting powder can be redispersed at any convenient time into a suitable aqueous medium such as saline, buffered saline, water, buffered aqueous media, solutions of amino acids, solutions of vitamins, solutions of carbohydrates, or the like, as well as combinations of any two or more thereof, to obtain a suspension that can be administered to mammals. Methods contemplated for obtaining this powder include freeze-drying, spray drying, and the like.

In accordance with a specific embodiment of the present invention, there is provided a method for the formation of unusually small submicron particles (nanoparticles), i.e., particles which are less than 200 nanometers in diameter. Such particles are capable of being sterile-filtered before use in the form of a liquid suspension. The ability to sterile-filter the end product of the invention formulation process (i.e., the drug particles) is of great importance since it is impossible to sterilize dispersions which contain high concentrations of protein (e.g., serum albumin) by conventional means such as autoclaving.

In order to obtain sterile-filterable particles (i.e., particles <200 nm), the pharmacologically active agent is initially dissolved in a substantially water immiscible organic solvent (e.g., a solvent having less than about 5% solubility in water, such as, for example, chloroform) at high concentration, thereby forming an oil phase containing the pharmacologically active agent. Suitable solvents are set forth above. Unlike conventional methods for nanoparticle formation, a polymer (e.g. polylactic acid) is not dissolved in the solvent. The oil phase employed in the process of the present invention contains only the pharmacologically active agent dissolved in solvent.

Next, a water miscible organic solvent (e.g., a solvent having greater than about 10% solubility in water, such as, for example, ethanol) is added to the oil phase at a final concentration in the range of about 1%–99% v/v, more preferably in the range of about 5%–25% v/v of the total organic phase. The water miscible organic solvent can be selected from such solvents as ethyl acetate, ethanol, tetrahydrofuran, dioxane, acetonitrile, acetone, dimethyl sulfoxide, dimethyl formamide, methyl pyrrolidinone, and the like. alternatively, the mixture of water immiscible solvent with the water miscible solvent is prepared first, followed by dissolution of the pharmaceutically active agent in the mixture.

Next, human serum albumin or any other suitable stabilizing agent as described above is dissolved in aqueous media. This component acts as a stabilizing agent for the formation of stable nanodroplets. Optionally, a sufficient amount of the first organic solvent (e.g. chloroform) is dissolved in the aqueous phase to bring it close to the saturation concentration. A separate, measured amount of the organic phase (which now contains the pharmacologically active agent, the first organic solvent and the second organic solvent) is added to the saturated aqueous phase, so that the phase fraction of the organic phase is between about 0.5%–015% v/v, and more preferably between 1% and 8% v/v.

Next, a mixture composed of micro and nanodroplets is formed by homogenization at low shear forces. This can be accomplished in a variety of ways, as can readily be identified by those of skill in the art, employing, for example, a conventional laboratory homogenizer operated in the range of about 2,000 up to about 15,000 rpm. This is followed by homogenization under high pressure (i.e., in the range of about 3,000 up to 30,000 psi). The resulting mixture comprises an aqueous protein solution (e.g., human serum albumin), the water insoluble pharmacologically active agent, the first solvent and the second solvent. Finally, solvent is rapidly evaporated under vacuum to yield a colloidal dispersion system (pharmacologically active agent and protein) in the form of extremely small nanoparticles (i.e., particles in the range of about 10 nm–200 nm diameter), and thus can be sterile-filtered. The preferred size range of the particles is between about 50 nm–170 nm, depending on the formulation and operational parameters.

Colloidal systems prepared in accordance with the present invention may be further converted into powder form by removal of the water therefrom, e.g., by lyophilization at a suitable temperature-time profile. The protein (e.g., human serum albumin) itself acts as a cryoprotectant, and the powder is easily reconstituted by addition of water, saline or buffer, without the need to use such conventional cryoprotectants as mannitol, sucrose, glycine, and the like. While not required, it is of course understood that conventional cryoprotectants may be added to invention formulations if so desired.

The polymeric shell containing solid or liquid cores of pharmacologically active agent allows for the delivery of high doses of the pharmacologically active agent in relatively small volumes. This minimizes patient discomfort at receiving large volumes of fluid and minimizes hospital stay. In addition, the walls of the polymeric shell or coating are generally completely degradable in vivo by proteolytic enzymes (e.g., when the polymer is a protein), resulting in no side effects from the delivery system as is the case with current formulations.

According to this embodiment of the present invention, particles of substantially water insoluble pharmacologically active agents have a cross-sectional diameter of no greater than about 10 microns. A cross-sectional diameter of less than 5 microns is more preferred, while a cross-sectional diameter of less than 1 micron is presently the most preferred for the intravenous route of administration.

Substantially water insoluble pharmacologically active agents contemplated for use in the practice of the present invention include pharmaceutically active agents, diagnostic agents, agents of nutritional value, and the like. Examples of pharmaceutically active agents include:

analgesics/antipyretics (e.g., aspirin, acetaminophen, ibuprofen, naproxen sodium, buprenorphine hydrochloride, propoxyphene hydrochloride, propoxyphene napsylate, meperidine hydrochloride, hydromorphone hydrochloride, morphine sulfate, oxycodone hydrochloride, codeine phosphate, dihydrocodeine bitartrate, pentazocine hydrochloride, hydrocodone bitartrate, levorphanol tartrate, diflunisal, trolamine salicylate, nalbuphine hydrochloride, mefenamic acid, butorphanol tartrate, choline salicylate, butalbital, phenyltoloxamine citrate, diphenhydramine citrate, methotrimeprazine, cinnamedrine hydrochloride, meprobamate, and the like);

anesthetics (e.g., cyclopropane, enflurane, halothane, isoflurane, methoxyflurane, nitrous oxide, propofol, and the like);

antiasthamatics (e.g., Azelastine, Ketotifen, Traxanox, and the like);

antibiotics (e.g., neomycin, streptomycin, chloramphenicol, cephalosporin, ampicillin, penicillin, tetracycline, and the like);

antidepressants (e.g., nefopam, oxypertine, doxepin hydrochloride, amoxapine, trazodone hydrochloride, amitriptyline hydrochloride, maprotiline hydrochloride, phenelzine sulfate, desipramine hydrochloride, nortriptyline hydrochloride, tranylcypromine sulfate, fluoxetine hydrochloride, doxepin hydrochloride, imipramine hydrochloride, imipramine pamoate, nortriptyline, amitriptyline hydrochloride, isocarboxazid, desipramine hydrochloride, trimipramine maleate, protriptyline hydrochloride, and the like);

antidiabetics (e.g., biguanides, hormones, sulfonylurea derivatives, and the like);

antifungal agents (e.g., griseofulvin, keloconazole, amphotericin B, Nystatin, candicidin, and the like);

antihypertensive agents (e.g., propanolol, propafenone, oxyprenolol, Nifedipine, reserpine, trimethaphan camsylate, phenoxybenzamine hydrochloride, pargyline hydrochloride, deserpidine, diazoxide, guanethidine monosulfate, minoxidil, rescinnamine, sodium nitroprusside, rauwolfia serpentina, alseroxylon, phentolamine mesylate, reserpine, and the like);

anti-inflammatories (e.g., (non-steroidal) indomethacin, naproxen, ibuprofen, ramifenazone, piroxicam, (steroidal) cortisone, dexamethasone, fluazacort, hydrocortisone, prednisolone, prednisone, and the like);

antineoplastics (e.g., adriamycin, cyclophosphamide, actinomycin, bleomycin, duanorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxol and derivatives thereof, taxotere and derivatives thereof, vinblastine, vincristine, tamoxifen, etoposide, piposulfan, and the like);

antianxiety agents (e.g., lorazepam, buspirone hydrochloride, prazepam, chlordiazepoxide hydrochloride, oxazepam, clorazepate dipotassium, diazepam, hydroxyzine pamoate, hydroxyzine hydrochloride, alprazolam, droperidol, halazepam, chlormezanone, dantrolene, and the like);

immunosuppressive agents (e.g., cyclosporine, azathioprine, mizoribine, FK506 (tacrolimus), and the like); antimigraine agents (e.g., ergotamine tartrate, propanolol hydrochloride, isometheptene mucate, dichloralphenazone, and the like);

sedatives/hypnotics (e.g., barbiturates (e.g., pentobarbital, pentobarbital sodium, secobarbital sodium), benzodiazapines (e.g., flurazepam hydrochloride, triazolam, tomazeparm, midazolam hydrochloride, and the like);

antianginal agents (e.g., beta-adrenergic blockers, calcium channel blockers (e.g., nifedipine, diltiazem hydrochloride, and the like), nitrates (e.g., nitroglycerin, isosorbide dinitrate, pentaerythritol tetranitrate, erythrityl tetranitrate, and the like));

antipsychotic agents (e.g., haloperidol, loxapine succinate, loxapine hydrochloride, thioridazine, thioridazine hydrochloride, thiothixene, fluphenazine hydrochloride, fluphenazine decanoate, fluphenazine enanthate, trifluoperazine hydrochloride, chlorpromazine hydrochloride, perphenazine, lithium citrate, prochlorperazine, and the like);

antimanic agents (e.g., lithium carbonate);

antiarrhythmics (e.g., bretylium tosylate, esmolol hydrochloride, verapamil hydrochloride, amiodarone, encainide hydrochloride, digoxin, digitoxin, mexiletine hydrochloride, disopyramide phosphate, procainamide hydrochloride, quinidine sulfate, quinidine gluconate, quinidine polygalacturonate, flecainide acetate, tocainide hydrochloride, lidocaine hydrochloride, and the like);

antiarthritic agents (e.g., phenylbutazone, sulindac, penicillamine, salsalate, piroxicam, azathioprine, indomethacin, meclofenamate sodium, gold sodium thiomalate, ketoprofen, auranofin, aurothioglucose, tolmetin sodium, and the like);

antigout agents (e.g., colchicine, allopurinol, and the like);

anticoagulants (e.g., heparin, heparin sodium, warfarin sodium, and the like);

thrombolytic agents (e.g., urokinase, streptokinase, altoplase, and the like);

antifibrinolytic agents (e.g., aminocaproic acid);

hemorheologic agents (e.g., pentoxifylline);

antiplatelet agents (e.g., aspirin, empirin, ascriptin, and the like);

anticonvulsants (e.g., valproic acid, divalproate sodium, phenytoin, phenytoin sodium, clonazepam, primidone, phenobarbitol, phenobarbitol sodium, carbamazepine, amobarbital sodium, methsuximide, metharbital, mephobarbital, mephenytoin, phensuximide, paramethadione, ethotoin, phenacemide, secobarbitol sodium, clorazepate dipotassium, trimethadione, and the like);

antiparkinson agents (e.g., ethosuximide, and the like);

antihistamines/antipruritics (e.g., hydroxyzine hydrochloride, diphenhydramine hydrochloride, chlorpheniramine maleate, brompheniramine maleate, cyproheptadine hydrochloride, terfenadine, clemastine fumarate, triprolidine hydrochloride, carbinoxamine maleate, diphenylpyraline hydrochloride, phenindamine tartrate, azatadine maleate, tripelennamine hydrochloride, dexchlorpheniramine maleate, methdilazine hydrochloride, trimprazine tartrate and the like);

agents useful for calcium regulation (e.g., calcitonin, parathyroid hormone, and the like);

antibacterial agents (e.g., amikacin sulfate, aztreonam, chloramphenicol, chloramphenicol palmitate, chloramphenicol sodium succinate, ciprofloxacin hydrochloride, clindamycin hydrochloride, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, colistin sulfate, and the like);

antiviral agents (e.g., interferon gamma, zidovudine, amantadine hydrochloride, ribavirin, acyclovir, and the like);

antimicrobials (e.g., cephalosporins (e.g., cefazolin sodium, cephradine, cefaclor, cephapirin sodium, ceftizoxime sodium, cefoperazone sodium, cefotetan disodium, cefutoxime azotil, cefotaxime sodium, cefadroxil monohydrate, ceftazidime, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, cefuroxime sodium, and the like), penicillins (e.g., ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G potassium, penicillin G procaine, methicillin sodium, nafcillin sodium, and the like), erythromycins (e.g., erythromycin ethylsuccinate, erythromycin, erythromycin estolate, erythromycin lactobionate, erythromycin siearate, erythromycin ethylsuccinate, and the like), tetracyclines (e.g., tetracycline hydrochloride, doxycycline hyclate, minocycline hydrochloride, and the like), and the like);

anti-infectives (e.g., GM-CSF);

bronchodialators (e.g., sympathomimetics (e.g., epinephrine hydrochloride, metaproterenol sulfate, terbutaline sulfate, isoetharine, isoetharine mesylate, isoetharine hydrochloride, albuterol sulfate, albuterol, bitolterol, mesylate isoproterenol hydrochloride, terbutaline sulfate, epinephrine bitartrate, metaproterenol sulfate, epinephrine, epinephrine bitartrate), anticholinergic agents (e.g., ipratropium bromide), xanthines (e.g., aminophylline, dyphylline, metaproterenol sulfate, aminophylline), mast cell stabilizers (e.g., cromolyn sodium), inhalant corticosteroids (e.g., flurisolidebeclomethasone dipropionate, beclomethasone dipropionate monohydrate), salbutamol, beclomethasone dipropionate (BDP), ipratropium bromide, budesonide, ketotifen, salmeterol, xinafoate, terbutaline sulfate, triamcinolone, theophylline, nedocromil sodium, metaproterenol sulfate, albuterol, flunisolide, and the like);

hormones (e.g., androgens (e.g., danazol, testosterone cypionate, fluoxymesterone, ethyltostosterone, testosterone enanihate, methyltestosterone, fluoxymesterone, testosterone cypionate), estrogens (e.g., estradiol, estropipate, conjugated estrogens), progestins (e.g., methoxyprogesterone acetate, norethindrone acetate), corticosteroids (e.g., triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate methylprednisolone sodium succinate, hydrocortisone sodium succinate, methylprednisolone sodium succinate, triamcinolone hexacatonide, hydrocortisone, hydrocortisone cypionate, prednisolone, fluorocortisone acetate, paramethasone acetate, prednisolone tebulate, prednisolone acetate, prednisolone sodium phosphate, hydrocortisone sodium succinate, and the like), thyroid hormones (e.g., levothyroxine sodium) and the like), and the like;

hypoglycemic agents (e.g., human insulin, purified beef insulin, purified pork insulin, glyburide, chlorpropamide, glipizide, tolbutamide, tolazamide, and the like);

hypolipidemic agents (e.g., clofibrate, dextrothyroxine sodium, probucol, lovastatin, niacin, and the like);

proteins (e.g., DNase, alginase, superoxide dismutase, lipase, and the like);

nucleic acids (e.g., sense or anti-sense nucleic acids encoding any therapeutically useful protein, including any of the proteins described herein, and the like);

agents useful for erythropoiesis stimulation (e.g., erythropoietin);

antiulcer/antireflux agents (e.g., famotidine, cimetidine, ranitidine hydrochloride, and the like);

antinauseants/antiemetics (e.g., meclizine hydrochloride, nabilone, prochlorperazine, dimenhydrinate, promethazine hydrochloride, thiethylperazine, scopolamine, and the like);

oil-soluble vitamins (e.g., vitamins A, D, E, K, and the like);

as well as other drugs such as mitotane, visadine, halonitrosoureas, anthrocyclines, ellipticine, and the like.

Examples of diagnostic agents contemplated for use in the practice of the present invention include ultrasound contrast agents, radiocontrast agents (e.g., iodo-octanes, halocarbons, renografin, and the like), magnetic contrast agents (e.g., fluorocarbons, lipid soluble paramagnetic compounds, and the like), as well as other diagnostic agents which cannot readily be delivered without some physical and/or chemical modification to accommodate the substantially water insoluble nature thereof.

Examples of agents of nutritional value contemplated for use in the practice of the present invention include amino acids, sugars, proteins, carbohydrates, fat-soluble vitamins (e.g., vitamins A, D, E, K, and the like) or fat, or combinations of any two or more thereof.

A number of biocompatible polymers may be employed in the practice of the present invention for the formation of the polymeric shell which surrounds the substantially water insoluble pharmacologically active agents. Essentially any polymer, natural or synthetic, optionally bearing sulfhydryl groups or disulfide bonds within its structure may be utilized for the preparation of a disulfide crosslinked shell about particles of substantially water insoluble pharmacologically active agents. The sulfhydryl groups or disulfide linkages may be preexisting within the polymer structure or they may be introduced by a suitable chemical modification. For example, natural polymers such as proteins, peptides, polynucleic acids, polysaccharides (e.g., starch, cellulose, dextrans, alginates, chitosan, pectin, hyaluronic acid, and the like), proteoglycans, lipoproteins, and so on, are candidates for such modification.

Proteins contemplated for use as stabilizing agents in accordance with the present invention include albumins (which contain 35 cysteine residues), immunoglobulins, caseins, insulins (which contain 6 cysteines), hemoglobins (which contain 6 cysteine residues per $\alpha_2\beta_2$ unit), lysozymes (which contain 8 cysteine residues), immunoglobulins, $\alpha$-2-macroglobulin, fibronectins, vitronectins, fibrinogens, lipases, and the like. Proteins, peptides, enzymes, antibodies and combinations thereof, are general classes of stabilizers contemplated for use in the present invention.

A presently preferred protein for use in the formation of a polymeric shell is albumin. Optionally, proteins such as $\alpha$-2-macroglobulin, a known opsonin, could be used to enhance uptake of the shell encased particles of substantially water insoluble pharmacologically active agents by macrophage-like cells, or to enhance the uptake of the shell encased particles into the liver and spleen. Specific antibodies may also be utilized to target the nanoparticles to specific locations.

Similarly, synthetic polypeptides containing cysteine residues are also good candidates for formation of a shell about the substantially water insoluble pharmacologically active agents. In addition, polyvinyl alcohol, polyhydroxyethyl methacrylate, polyacrylic acid, polyethyloxazoline, polyacrylamide, polyvinyl pyrrolidinone, and the like, are good candidates for chemical modification (for example, by the introduction of sulfhydryl and/or disulfide linkages) and shell formation (by causing the crosslinking thereof). Thus, for example, contemplated for use in the practice of the present invention are such materials as synthetic polyamino acids containing cysteine residues and/or disulfide groups; polyvinyl alcohol modified to contain free sulfhydryl groups and/or disulfide groups; polyhydroxyethyl methacrylate modified to contain free sulfhydryl groups and/or disulfide groups; polyacrylic acid modified to contain free sulfhydryl groups and/or disulfide groups; polyethyloxazoline modified to contain free sulfhydryl groups and/or disulfide groups; polyacrylamide modified to contain free sulfhydryl groups and/or disulfide groups; polyvinyl pyrrolidinone modified to contain free sulfhydryl groups and/or disulfide groups; polyalkylene glycols modified to contain free sulfhydryl groups and/or disulfide groups; polylactides, polyglycolides, polycaprolactones, or copolymers thereof, modified to contain free sulfhydryl groups and/or disulfide groups; as well as mixtures of any two or more thereof.

In the preparation of invention compositions, a wide variety of organic media can be employed to suspend or dissolve the substantially water insoluble pharmacologically active agent. Organic media contemplated for use in the practice of the present invention include any nonaqueous liquid that is capable of suspending or dissolving the pharmacologically active agent, but does not chemically react with either the polymer employed to produce the shell, or the pharmacologically active agent itself. Examples include vegetable oils (e.g., soybean oil, olive oil, and the like), coconut oil, safflower oil, cotton seed oil, sesame oil, orange oil, limonene oil, aliphatic, cycloaliphatic, or aromatic hydrocarbons having 4–30 carbon atoms (e.g., n-dodecane, n-decane, n-hexane, cyclohexane, toluene, benzene, and the like), aliphatic or aromatic alcohols having 2–30 carbon atoms (e.g., octanol, and the like), aliphatic or aromatic esters having 2–30 carbon atoms (e.g., ethyl caprylate (octanoate), and the like), alkyl, aryl, or cyclic ethers having 2–30 carbon atoms (e.g., diethyl ether, tetrahydrofuran, and the like), alkyl or aryl halides having 1–30 carbon atoms (and optionally more than one halogen substituent, e.g., $CH_3Cl$ $CH_2Cl_2$, $CH_2Cl$–$CH_2Cl$, and the like), ketones having 3–30 carbon atoms (e.g., acetone, methyl ethyl ketone, and the like), polyalkylene glycols (e.g., polyethylene glycol, and the like), or combinations of any two or more thereof.

Especially preferred combinations of organic media contemplated for use in the practice of the present invention typically have a boiling point of no greater than about 200° C., and include volatile liquids such as dichloromethane, chloroform, ethyl acetate, benzene, and the like (i.e., solvents that have a high degree of solubility for the pharmacologically active agent, and are soluble in the other organic medium employed), along with a higher molecular weight (less volatile) organic medium. When added to the other organic medium, these volatile additives help to drive the solubility of the pharmacologically active agent into the organic medium. This is desirable since this step is usually time consuming. Following dissolution, the volatile component may be removed by evaporation (optionally under vacuum).

Particles of pharmacologically active agent associated with a polymeric shell, prepared as described above, are delivered as a suspension in a biocompatible aqueous liquid. This liquid may be selected from water, saline, a solution containing appropriate buffers, a solution containing nutritional agents such as amino acids, sugars, proteins, carbohydrates, vitamins or fat, and the like.

Those skilled in the art will recognize that several variations are possible within the scope and spirit of this invention. The organic medium within the polymeric shell may be varied, a large variety of pharmacologically active agents may be utilized, and a wide range of proteins as well as other natural and synthetic polymers may be used in the formation of the walls of the polymeric shell. Applications are also fairly wide ranging. Other than biomedical applications such as the delivery of drugs, diagnostic agents (in imaging applications), artificial blood and parenteral nutritional agents, the polymeric shell structures of the invention may be incorporated into cosmetic applications such as skin creams or hair care products, in perfumery applications, in pressure sensitive inks, and the like.

The invention will now be described in greater detail by reference to the following non-limiting examples.

EXAMPLE 1

Preparation of Nanoparticles by High Pressure Homogenization 30 mg paclitaxel is dissolved in 3.0 ml methylene chloride. The solution was added to 27.0 ml of human serum abumin solution (1% w/v). The mixture was homogenized for 5 minutes at low RPM (Vitris homogenizer, model:

Tempest I. Q.) in order to form a crude emulsion, and then transferred into a high pressure homogenizer (Avestin). The emulsification was performed at 9000–18,000 psi while recycling the emulsion for at least 5 cycles. The resulting system was transferred into a Rotary evaporator, and methylene chloride was rapidly removed at 40° C., at reduced pressure (30 mm Hg), for 20–30 minutes. The resulting dispersion was translucent, and the typical diameter of the resulting paclitaxel particles was 160–220 (Z-average, Malvern Zetasizer).

The dispersion was further lyophilized for 48 hrs. without adding any cryoprotectant. The resulting cake could be easily reconstituted to the original dispersion by addition of sterile water or saline. The particle size after reconstitution was the same as before lyophilization.

EXAMPLE 2

Preparation of Nanoparticles by Sonication

The purpose of this example is to demonstrate the formation of nanoparticles of Paclitaxel by using cavitation and high shear forces during a sonication process. Thus, 20 mg paclitaxel is dissolved in 1.0 ml methylene chloride. The solution is added to 4.0 ml of human serum abumin solution (5% w/v). The mixture is homogenized for 5 minutes at low RPM (Vitris homogenizer, model: Tempest I.Q.) in order to form a crude emulsion, and then transferred into a 40 kHz sonicator cell. The sonicator is performed at 60–90% power at 0 degree for 1 min (550 Sonic Dismembrator). The mixture is transferred into a Rotary evaporator, and methylene chloride is rapidly removed at 40° C., at reduced pressure (30 mm Hg), for 20–30 minutes. The typical diameter of the resulting paclitaxel particles was 350–420 nm (Z-average, Malvern Zetasizer).

The dispersion was further lyophilized for 48 hrs. without adding any cryoprotectant. The resulting cake could be easily reconstituted to the original dispersion by addition of sterile water or saline. The particle size after reconstitution was the same as before lyophilization.

EXAMPLE 3

Use of Conventional Surfactants and Proteins Results in formation of Large crystals The following example demonstrates the effect of adding surfactants which are used in the conventional solvent evaporation method. A series of experiments was conducted employing a similar procedure to that described in Example 1, but a surfactant such as Tween 80 (1% to 10%) is added to the organic solvent. It was found that after removal of the methylene chloride, a large number of paclitaxel crystals is obtained having an average size of 1–2 micron, as viewed by light microscopy and under polarized light. The crystals grow within a few hours to form very large needle-like crystals, with a size in the range of about 5–15 micron. A similar phenomenon is observed with other commonly used surfactants, such as Pluronic F-68, Pluronic F 127, Cremophor EL and Brij 58.

From these results it can be concluded that the conventional solvent evaporation method utilizing conventional surfactants in combination with a protein such as albumin is not suitable for the formation of submicron drug particles (e.g. Paclitaxel) without a polymeric core, while using a polar solvent (e.g., methylene chloride).

EXAMPLE 4

Use of Conventional Surfactants Alone Results in formation of Large crystals

This example demonstrates that it is not possible to form nanoparticles while using conventional surfactants, without a polymeric core material, with pharmacologically active agents which are soluble in polar, water immiscible solvents (e.g. chloroform).

30 mg Taxol is dissolved in 0.55 ml chloroform and 0.05 ml ethanol. The solution is added to 29.4 ml of Tween 80 solution (1% w/v), which is presaturated with 1% chloroform. The mixture is homogenized for 5 minutes at low RPM (Vitris homogenizer, model: Tempest I. Q.) in order to form a crude emulsion, and then transferred into a high pressure homogenizer (Avestin). The emulsification is performed at 9000–18,000 psi while recycling the emulsion for at least 6 cycles. The resulting system was transferred into a Rotary evaporator, and the chloroform was rapidly removed at 40° C., at reduced pressure (30 mm Hg), for 15–30 minutes. The resulting dispersion was opaque, and contained large needle-like crystals of the drug. The initial size of the crystals (observed also by polarized light), was 0.7–5 micron. Storage of the dispersion for several hours at room temperature led to further increase in crystal size, and ultimately to precipitation.

EXAMPLE 5

Preparation of Less than 200 nm Sterile-Filterable Nanoparticles

This example describes the process by which sterile-filterable drug particles can be obtained. Thus, 30 mg Taxol is dissolved in 0.55 ml chloroform and 0.05 ml ethanol. The solution is added to 29.4 ml of human serum abumin solution (1% w/v), which is presaturated with 1% chloroform. The mixture is homogenized for 5 minutes at low RPM (Vitris homogenizer, model: Tempest I. Q.) in order to form a crude emulsion, and then transferred into a high pressure homogenizer (Avestin). The emulsification is performed at 9000–18,000 psi while recycling the emulsion for at least 6 cycles. The resulting system is transferred into a Rotary evaporator, and the chloroform is rapidly removed at 40° C., at reduced pressure (30 mm Hg), for 15–30 minutes. The resulting dispersion is translucent, and the typical diameter of the resulting Taxol particles is 140–160 nm (Z-average, Malvern Zeta Sizer). The dispersion is filtered through a 0.22 micron filter (Millipore), without any significant change in turbidity, or particle size. HPLC analysis of the Taxol content revealed that more than 97% of the Taxol was recovered after filtration, thus providing a sterile Taxol dispersion.

The sterile dispersion was further lyophilized for 48 hrs. without adding any cryoprotectant. The resulting cake could be easily reconstituted to the original dispersion by addition of sterile water or saline. The particle size after reconstitution was the same as before lyophilization.

EXAMPLE 6

Preparation of Less than 200 nm Sterile-Filterable Nanoparticles

This example describes the process by which sterile-filterable drug particles can be obtained. Thus, 225 mg Taxol is dissolved in 2.7 ml chloroform and 0.3 ml ethanol. The solution is added to 97 ml of human serum abumin solution (3% w/v). The mixture is homogenized for 5 minutes at low RPM (Vitris homogenizer, model: Tempest I. Q.) in order to form a crude emulsion, and then transferred into a high pressure homogenizer (Avestin). The emulsification is performed at 9000–18,000 psi while recycling the emulsion for at least 6 cycles. The resulting system is transferred into a Rotary evaporator, and the chloroform is rapidly removed at 400° C., at reduced pressure (30 mm Hg), for 15–30 minutes. The resulting dispersion is translucent, and the typical diameter of the resulting Taxol particles is 140–160 nm (Z-average, Malvern Zeta Sizer). The dispersion is filtered through a 0.22 micron filter (Sartorius, sartobran 300), without any significant change in turbidity, or particle size. HPLC analysis of the Taxol content typically revealed that 70–100% of the Taxol could be recovered after filtration, depending on the conditions employed. Thus, a sterile Taxol dispersion was obtained.

The sterile dispersion was aseptically filled into sterile glass vials and lyophilized without adding any cryoprotectant. The resulting cake could be easily reconstituted to the original dispersion by addition of sterile water or saline. The particle size after reconstitution was the same as before lyophilization.

EXAMPLE 7

Effect of Phase Fraction of Organic Solvent on Particle size

The following example demonstrates the importance of having an unusually low phase fraction of the organic solvent in the system.

Thus, a series of experiments was conducted following a similar procedure to that described for Example 5, except the phase fraction of the organic solvent was altered, and the ethanol content maintained at 10% v/v in the organic phase. It was found that increasing the phase fraction led to a significant increase in particle size: at 4% v/v phase fraction (above the saturation concentration, or 5% v/v total chloroform concentration) the resulting particles have a diameter of 250 nm; at 3% v/v phase fraction, the particles have a 200 nm diameter, and at 2% v/v phase fraction, the particles have a 150 nm diameter.

Clearly, only the particles prepared at very low phase fraction could be sterile-filtered.

EXAMPLE 8

Effect of Drug Concentration on Particle Size

The role of drug concentration in the organic phase is demonstrated in the following example. Two experiments were performed in which the Taxol concentration in the organic phase was 50 mg/ml or 75 mg/ml, while all other parameters were the same as described in Example 3. It was found that the low drug concentration yielded particles having a diameter of about 150 nm, while those prepared at the higher drug loading were smaller, i.e., 130–138 nm. When a similar experiment was performed, but with an ethanol concentration in the organic phase of about 50%, a similar trend was observed, i.e., particles were 210 nm and 156 nm in diameter, for 25 mg/ml and 50 mg/ml drug concentration, respectively.

These findings directly contradict those reported by Sjostrom et al., supra, for the formation of nanoparticles in presence of surfactants.

EXAMPLE 9

Nanoparticle formation of a model Drug 30 mg Isoreserpine (a model drug) is dissolved in 3.0 ml methylene chloride. The solution is added to 27.0 ml of human serum abumin solution (1% w/v). The mixture is homogenized for 5 minutes at low RPM (Vitris homogenizer, model: Tempest I. Q.) in order to form a crude emulsion, and then transferred into a high pressure homogenizer (Avestin). The emulsification is performed at 9000–18,000 psi while recycling the emulsion for at least 5 cycles. The resulting system is transferred into a Rotary evaporator, and methylene chloride is rapidly removed at 40° C., at reduced pressure (30 mm Hg), for 20–30 minutes. The resulting dispersion is translucent, and the typical diameter of the resulting paclitaxel particles was 120–140 nm (Z-average, Malvern Zetasizer). The dispersion was filtered through a 0.22 micron filter (Millipore).

The sterile dispersion was further lyophilized for 48 hrs. without adding any cryoprotectant. The resulting cake could be easily reconstituted to the original dispersion by addition of sterile water or saline. The particle size after reconstitution was the same as before lyophilization.

EXAMPLE 10

Extremely Small particle formation with a model drug

The effect of ethanol addition on reducing particle size is demonstrated for Isoreserpine. Thus, 30 mg Isoreserpine is dissolved in 2.7 ml methylene chloride and 0.3 ml ethanol. The solution is added to 27.0 ml of human serum abumin solution (1% w/v). The mixture is homogenized for 5 minutes at low RPM (Vitris homogenizer, model: Tempest I. Q.) in order to form a crude emulsion, and then transferred into a high pressure homogenizer (Avestin). The emulsification was performed at 9000–18,000 psi while recycling the emulsion for at least 5 cycles. The resulting system was transferred into a Rotary evaporator, and methylene chloride was rapidly removed at 40° C., at reduced pressure (30 mm Hg), for 20–30 minutes. The resulting dispersion was translucent, and the typical diameter of the resulting paclitaxel particles was 90–110 nm (Z-average, Malvern Zetasizer). The dispersion was filtered through a 0.22 micron filter (Millipore).

The sterile dispersion was further lyophilized for 48 hrs. without adding any cryoprotectant. The resulting cake could be easily reconstituted to the original dispersion by addition of sterile water or saline. The particle size after reconstitution was the same as before lyophilization.

EXAMPLE 11

Use of a Water miscible Solvent alone, supersaturated with drug—Not suitable for invention process 30 mg Taxol is dispersed in 0.6 ml ethanol. At this concentration (50 mg/ml), the taxol is not completely soluble and forms a supersaturated dispersion. The dispersion is added to 29.4 ml of human serum abumin solution (1% w/v). The mixture is homogenized for 5 minutes at low RPM (Vitris homogenizer, model: Tempest I. Q.) in order to form a crude dispersion, and then transferred into a high pressure homogenizer (Avestin) The emulsification is performed at 9000–18,000 psi while recycling the emulsion for at least 6 cycles. The resulting system is transferred into a Rotary evaporator, and the ethanol is rapidly removed at 40° C., at reduced pressure (30 mm Hg), for 15–30 minutes. The resulting dispersion particle size is extremely broad, ranging from about 250 nm to several microns.

Observation under the microscope revealed the presence of large particles and typical needle shaped crystals of taxol.

These particles were too large for intravenous injection. This experiment demonstrates that the use of solvents such as ethanol that are freely miscible in water in the invention process results in the formation of large particles with very broad particle size distribution and as such cannot be used alone for the invention process. Thus the invention process specifically excludes the use of water miscible solvents when used alone for the dissolution or dispersion of the drug component. The invention process requires that such solvents, when used, must be mixed with essentially water immiscible solvents to allow production of the invention nanoparticles.

EXAMPLE 12

Use of a Water miscible Solvent alone containing dissolved drug—Not suitable for invention process 30 mg Taxol is dispersed in 1.3 ml ethanol. At this concentration (approx. 24.5 mg/ml), the taxol is completely soluble in ethanol. The solution is added to 28.7 ml of human serum abumin solution (1% w/v). The mixture is homogenized for 5 minutes at low RPM (Vitris homogenizer, model: Tempest I. Q.) in order to form a crude dispersion, and then transferred into a high pressure homogenizer (Avestin). The emulsification is performed at 9000–18,000 psi while recycling the emulsion for at least 6 cycles. The resulting system is transferred into a Rotary evaporator, and the ethanol is rapidly removed at 40° C., at reduced pressure (30 mm Hg), for 15–30 minutes. The resulting dispersion particle size was extremely broad, ranging from about 250 nm to several microns. Observation under the microscope revealed the presence of large particles and typical needle shaped crystals of taxol. These particles were too large for intravenous injection.

This example, in addition to Example 11 above, demonstrates that the use in the invention process of solvents such as ethanol that are freely miscible in water results in the formation of large particles with very broad particle size distribution and as such cannot be used alone for the invention process. Thus the invention process specifically excludes the use of water miscible solvents when used alone for the dissolution or dispersion of the drug component. The invention process requires that such solvents, when used, be mixed with essentially water immiscible solvents to enable formation of invention nanoparticles.

EXAMPLE 13

Determination of Physical State of Paclitaxel in Nanoparticle Form by X-Ray Powder Diffraction Paclitaxel raw material is usually present as needle shaped crystald of varying sizes typically between 5–500 microns. The presence of crystals in a drug formulation for intravenous injection is obviously detrimental if crystals are present in size above a few microns due to potential blockage of capillaries. In addition, the solubility of drug crystals in general would be lower than for amorphous drug, thereby lowering the bioavailability of the drug following intravenous administration. It is also known that as the loading of the drug in a formulation is increased, the tendency for crystallization also increases. Thus it is advantageous that the formulation contain the drug in essentially amorphous form.

X-Ray powder diffraction was used to determine the crystalline or non-crystalline nature of paclitaxel in the lyophilized powder formulation. The following samples were analyzed: Sample 1—Paclitaxel powder; Sample 2—Lyophilized serum albumin; Sample 3—a physical mixture of paclitaxel and albumin; and Sample 4—formulated paclitaxel. Each sample was x-rayed from 2° to 70° 2θ angles using CuKα radiation, an accelerating voltage of 40 KeV/30 mA, a step size of 0.050° 2θ and a data acquisition time of 2.0 seconds per step. Sample 1 showed strong peaks typical of a crystalline sample. The most intense paclitaxel peak was located at 5.10° 2θ. Sample 2 showed broad humps typical of amorphous material. Sample 3 showed largely the broad humps of Sample 2, but in addition, the peak at 5.10° 2θ of paclitaxel was visible. Sample 4, the formulated paclitaxel showed no evidence of crystallinity characteristic of paclitaxel and appeared identical to Sample 2, indicating the presence of substantially amorhpous pharmacologically active agent in the formulated sample.

The amorphous nature of the nanoparticles produced according to the invention stands in direct contrast to the products produced by other methods described in the art for producing nanoparticles. For example, the use of grinding techniques, as described in U.S. Pat. No. 5,145,684 (Liversidge et al.), and as described by Liversidge-Merisko et al., *Pharmaceutical Research* 13 (2):272–278 (1996), produces a substantially crystalline product.

EXAMPLE 14

Treatment of Tumors in an Animal Model with Paclitaxel Nanoparticles

Nanoparticles of paclitaxel (taxol) were prepared as described above in Example 1. This formulation of the drug was tested in a MX-1 human mammary tumor xenograft model in mice. The mice were implanted subcutaneously with the MX-1 mammary tumor and the treatment was initiated when the tumor reached approximately 150–300 mg in size. This occurred by day 12 and the treatment was initiated on day 13 after initial seeding.

Tumor bearing mice were treated with paclitaxel nanoparticles at a dose of 20 mg/kg, given by bolus intravenous injection as a suspension in saline for five consecutive days. The treated group included five animals. The control tumor bearing group of five animals received only saline on the same schedule. The size of the tumors was monitored as a function of time. The control group showed a tremendous increase in tumor weight. All the animals in this group were sacrificed between day 28 and day 39. The treatment group on the other hand showed remarkable efficacy as all animals had no measurable tumors by day 25. The animals in this group were all sacrificed on day 39, at which time they showed no evidence of recurrence and no evidence of tumor. The results are shown in FIG. 1.

EXAMPLE 15

Treatment of Rheumatoid Arthritis in an Animal Model with Paclitaxel Nanoparticles Collagen induced arthritis model in the Louvain rat was used to test the therapeutic effect of Paclitaxel nanoparticles on arthritis. The paw sizes of the experimental animals were monitored to evaluate the seriousness of arthritis.

Figure 2:
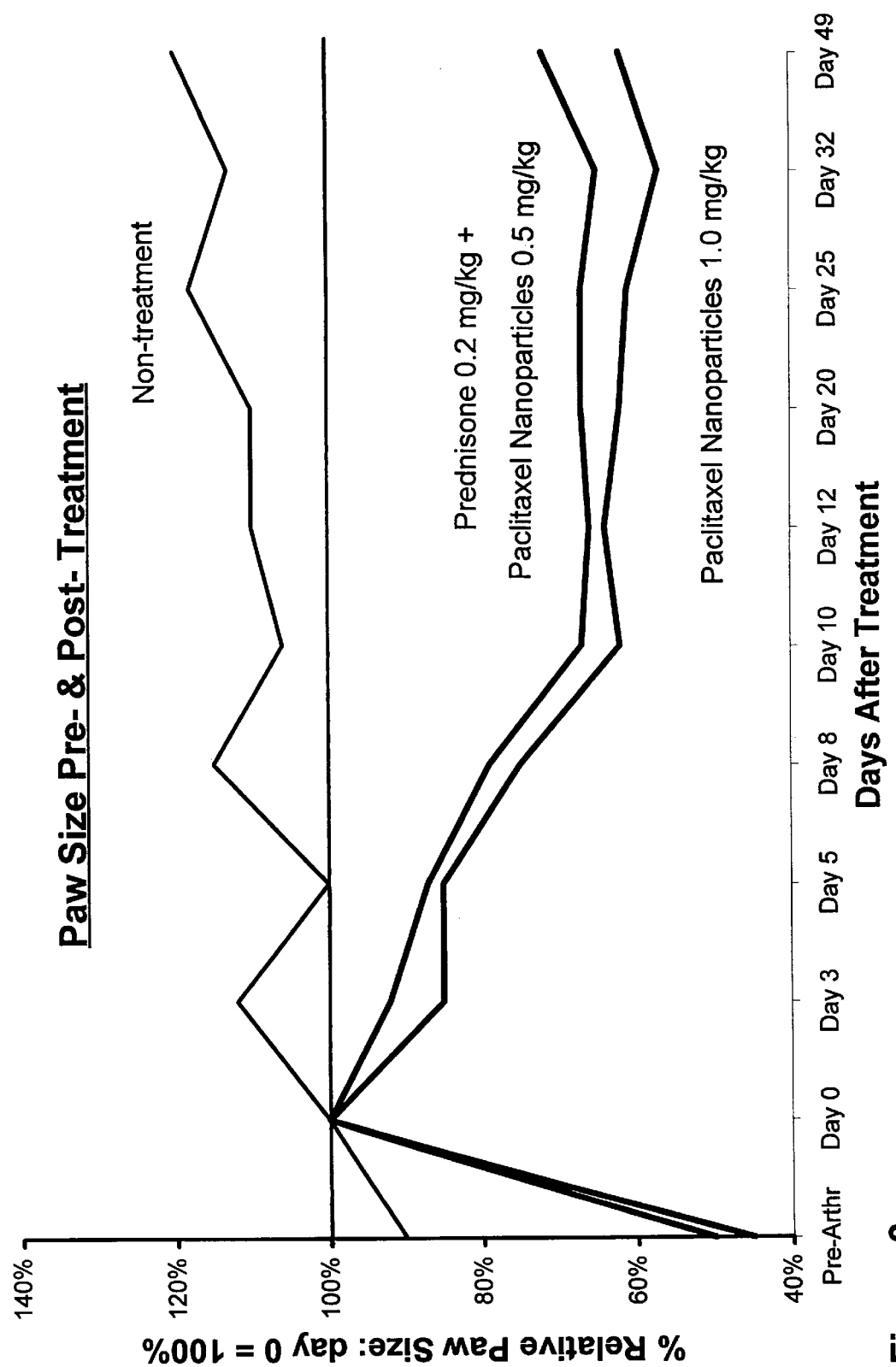
FIG. 2 presents the results of intraperitoneal administration of paclitaxel nanoparticles in rats that have developed arthritis in their paws following intradermal injection of collagen. Paw volumes are measured and indicate the severity of the disease. The paw volumes are normalized to 100% at the beginning of treatment. Day 0 represents the initiation of treatment. There are 3 groups—control group receiving saline (n=2, shown as a thin line and labelled in the figure a "non-treatment"); a first treatment group receiving paclitaxel nanoparticles at a dose of 1 mg/kg (n=4, shown as a heavy line and labelled in the figure as "paclitaxel nanoparticles 1.0 mg/kg"), and a second treatment group receiving combination therapy of paclitaxel nanoparticles at a dose of 0.5 mg/kg and prednisone at a dose of 0.2 mg/kg (n=4, shown as a heavy line and labelled in the figure as "prednisone 0.2 mg/kg+paclitaxel nanoparticles 0.5 mg/kg"). The two treatment groups show a dramatic reduction in paw volume with time, indicating a regression of arthritis, while the control group showed an increase in paw volume over the same period.

After the arthritis was fully developed (usually ~9–10 days after collagen injection), the experimental animals were divided into different groups to receive either Paclitaxel nanoparticles 1 mg/kg q.o.d, or Paclitaxel nanoparticles 0.5 mg/kg+Prednisone 0.2 mg/kg q.o.d. (combination treatment) intraperitoneally for 6 doses, then one dose per week for three weeks. The paw sizes were measured at the beginning of treatment (day 0) and every time the drug was injected. One group received only normal saline as control. By the end of the experiment, the group receiving Paclitaxel nanoparticles achieved a 42% reduction of paw size, the combination treatment group showed a 33% reduction of the paw size while the control group had about 20% increase of the paw size. Original paw size before arthritis was induced was 50%. The results are shown in FIG. 2.

In conclusion, the paclitaxel-containing nanoparticles demonstrated therapeutic effect on arthritis. To avoid side effects of long term use of both paclitaxel and the steroid, it is probably better to choose a combination treatment to get similar effect but only half the dosage of each drug.

EXAMPLE 16

In vivo Targeting of Nanoparticles

By incorporation of certain targeting moieties such as proteins, antibodies, enzymes, peptides, oligonucleotides, sugars, polysaccharides, and the like, into the protein coating of the nanoparticles, it is possible to target specific sites in the body. This targeting ability can be utilized for therapeutic or diagnostic purposes.

EXAMPLE 17

Intravenous Delivery Systems Formulated From a Variety of Materials

The materials used for the preparation of intravenous delivery systems may be polymeric (e.g., polyethylene, polyvinyl, polypropylene tubing, and the like), or glass. Standard medical grade tubing is known to contain hydrophobic moieties on the inner surfaces thereof. These moieties are thus available to come in contact with the injection solution. Indeed, such tubing is specifically tailored, as are the catheters, to present hydrophobic moieties in contact with the treatment solution so as to reduce the absorption of aqueous material to the tubing. However, any hydrophobic moieties in the treatment solution will likely bind to both the catheter tubing and other components of the delivery system. As a result, a substantial portion of a hydrophobic pharmacalogically active agent can become sequestered in the inner walls of the tubing catheter and delivery vessel. Consequently, the dosing of hydrophobic pharmacologically active agents can be erratic, since a substantial portion of the active agent can become absorbed to the walls of the tubing. In critical therapeutic treatments, where the hydrophobic pharmacologically active agent is used to treat a disease, a significant reduction in the effective dose of active agent can lead to a therapeutic failure. The failure is particularly striking when employing therapeutic moieties which require that the active agent be present above a certain level, yet the therapeutic window is narrow.

A novel method for the intravenous introduction of a hydrophobic pharmacologically active agent has now been developed. By protecting the hydrophobic moieties of the active agent, through association with the hydrophobic moieties of a biocompatible coating (e.g., albumin), the propensity of the active agent to become attached to the tubing is dramatically reduced. Thus, the present invention enables the use of highly hydrophobic drugs, in combination with standard medical grade polymers and hydrophobic glasses, in which the drug is protected and therefore not absorbed onto the surface. The invention method comprises placing a protective coating of a biocompatible polymer (e.g., albumin) around the hydrophobic drug and placing the resulting composition in a hydrophobic polymeric delivery system. The invention methods are therefore capable of improving the delivery of a variety of hydrophobic therapeutics.

EXAMPLE 18

Intravenous Administration of Therapeutics

Intravenous administration of therapeutics, for example, drugs, imaging agents, and the like, predisposes the therapeutic to at least one pass through the liver. As that therapeutic is filtered through the liver, a significant portion of that therapeutic is taken up and sequestered by the liver, and therefore, not available for systemic distribution. Moreover, once taken up by the liver, it is likely to be metabolized, and the resulting metabolic byproducts often have general systemic toxicities. By encapsulating the drug or other therapeutic agent in a coating according to the invention (e.g., using a protein such as albumin), liver sequestration upon intravenous administration is alleviated. Albumin, for example, is known to pass through the liver and become generally distributed throughout the patient. Thus, the sequestration of albumin by the liver does not occur to the same degree as toxic compounds or drugs which have hepatic receptors (or other mechanisms) which initiate processes which result in their removal from the blood stream. By protecting the therapeutic with a coating of a biocompatible polymer (e.g., a human albumin coating), the drug then bypasses the liver and is generally distributed through all organ systems. In accordance with one aspect of the present invention, there is provided a novel method for bypassing the liver, which comprises encapsulating a drug in a human liver albumin (essentially a physiological component). In this way, more of the drug becomes available for systemic therapy. In addition to the increased availability of the drug, there is a decrease in the production of metabolic byproducts of hepatocellular drug degradation. Both the increase in liver bypass and decrease in byproducts of drug metabolism provide a synergistic improvement in the overall drug efficacy. This improved efficacy extends to all drugs and materials that are encapsulated in human albumin.

EXAMPLE 19

Reducing Myelosuppressive Effects and General Toxicity of Drugs

Several chemotherapeutic drugs have dose limiting toxicity due to their myelosuppressive effects. Taxol (paclitaxel) is a classic example of such a drug. When administered in its currently approved formulation of cremaphor/ethanol, taxol produces myelosuppressive effects that limit the repeat administration of the drug and preclude retreatment of a patient for at least 3 weeks in order to allow blood counts of the patient to return to normal. It was postulated that due to the non-toxic compatible nature of the drug carrier of the present invention, viz. human albumin, the toxic side effect of myelosuppression may be greatly reduced.

Sprague dawley rats were given paclitaxel in commercial formulation (available from Bristol Myers Squibb (BMS) in cremaphor/ethanol) or prepared by the invention method as nanoparticles with albumin. Both formulations were administered by tail vein injection. A single dose level of 5 mg/kg was administered for the BMS formulation, whereas two dose levels of 5 mg/kg and 12 mg/kg were administered for the invention formulation (Capxol). The white blood cell counts of the rats were monitored daily after administration as an index of myelosuppression.

For the BMS formulation (5 mg/kg) it was found that the WBC counts dropped by 47.6% and 63.5% on day 1 and day 2 after administration, respectively, whereas for the Capxol formulation at 5 mg/kg, the WBC counts increased by 14.7% and 2.4% on day 1 and day 2, respectively. For the higher dose Capxol at 12 mg/kg, the WBC counts increased by 6.5% and 3.6% on day 1 and day 2, respectively.

These results indicate that short term myelosuppression is greatly reduced by administering the drug in the present invention formulation.

Another indicator of general toxicity is the body weight of the animal. Body weights of the rats were also monitored following administration of paclitaxel. At a dose of 5 mg/kg, the BMS formulation resulted in a reduction of body weight by 10.4% in 3 days following administration, whereas the same dose of paclitaxel administered in the invention formulation (Capxol) resulted in only a 3.9% drop in body weight, indicating the greatly reduced toxicity of the invention formulation.

EXAMPLE 20

Administration of Bolus dose of Nanoparticle Formulation

The anticancer drug, paclitaxel, in its commercial BMS formulation with Cremaphor/ethanol, cannot be administered as an intravenous bolus. This is due to the extensive toxicity of the vehicle which results in severe anaphylactic reactions and requires patients receiving the drug to be pre-medicated with steroids, antihistamines, and the like. The BMS formulation is administered as an intravenous infusion lasting anywhere from 1 hour to 24 hours. In contrast, formulations according to the present invention, due to the use of a non-toxic carrier, can be administered to a patient readily as an intravenous bolus (i.e., in a period less than 1 hour) without the toxicity problems seen in the BMS formulation that is used clinically today.

The effective dose of paclitaxel for a patient typically lies between 200–500 mg, depending on the patient body weight or body surface. The BMS formulation has to be administered at a final dosing concentration of 0.6 mg/ml, requiring large infusion volumes (typically in the range of about 300–1000 ml. In contrast, invention formulations (e.g., Capxol) do not have these limitations and can be administered at a desired concentration. This enables clinicians to treat patients by a rapid intravenous bolus that can be administered in as little as a few minutes. For example, if the invention formulation is reconstituted to a dosing concentration of 20 mg/ml, the infusion volume for a total dose of 200–500 mg is only 10–25 ml, respectively. This is a great advantage in clinical practice.

EXAMPLE 21

Reduction in Toxicity of Paclitaxel in the Nanoparticle Formulation Compared to the Commercial Cremaphor/Ethanol Formulation It is well known that the anticancer drug, paclitaxel, in its commercial BMS formulation with Cremaphor/ethanol, has extensive toxicity which results in severe anaphylactic reactions and requires patients receiving the drug to be pre-medicated with steroids, antihistamines, and the like. The toxicity of the BMS formulation was compared to the nanoparticle formulation of the present invention.

Thus, the formulations were injected intravenously through the tail vein of C57BL mice at different dose levels and toxic effects were monitored by general observation of mice after the injection.

For the BMS formulation, a dose of 30 mg/kg was uniformly lethal within 5 minutes of intravenous administration. For the same dose, the nanoparticle formulation according to the invention showed no apparent toxic effects. The nanoparticle formulation at a dose of 103 mg/kg showed some reduction in body weight of the mice, but even this high dose was not lethal. Doses of approximately 1000 mg/kg, 800 mg/kg and 550 mg/kg were all lethal but differing in time to lethality, which ranged between a few hours to 24 hours. The lethal dose of the invention formulation is greater than 103 mg/kg but less than 550 mg/kg.

Thus, the lethal dose of the invention formulation of paclitaxel is substantially higher than that of the commercial BMS formulation. This has great significance in clinical practice where higher doses of chemotherapeutic drugs may be administered for more effective oncolytic activity with greatly reduced toxicity.

EXAMPLE 22

Preparation of Nanoparticles of Cyclosporine (Capsorine I.V.) by High Pressure Homogenization 30 mg cyclosporine is dissolved in 3.0 ml methylene chloride. The solution is then added into 27.0 ml of human serum albumin solution (1% w/v). The mixture is homogenized for 5 minutes at low RPM (Vitris homogenizer model: Tempest I.Q.) in order to form a crude emulsion, and then transferred into a high pressure homogenizer (Avestin). The emulsification was performed at 9000–18,000 psi while recycling the emulsion for at least 5 cycles. The resulting system was transferred into a Rotavap and methylene chloride was rapidly removed at 40° C., at reduced pressure (30 mm Hg), for 20–30 minutes. The resulting dispersion was translucent and the typical diameter of the resulting cyclosporine particles was 160–220 (Z-average, Malvern Zetasizer).

The dispersion was further lyophilized for 48 hours, without adding any cryoprotectant. The resulting cake could be easily reconstituted to the original dispersion by addition of sterile water or saline. The particle size after reconstitution was the same as before lyophilization.

EXAMPLE 23

Preparation of Nanodroplets of Cyclosporine (Capsorine Oral) by High Pressure Homogenization 30 mg cyclosporine is dissolved in 3.0 ml of a suitable oil (sesame oil containing 10% orange oil). The solution is then added into 27.0 ml of human serum albumin solution (1% v/w). The mixture is homogenized for 5 minutes at low RPM (Vitris homogenizer, model: Tempest I.Q.) in order to form a crude emulsion, and then transferred into a high pressure homogenizer (Avestin). The emulsification is performed at 9000–18,000 psi while recycling the emulsion for at least 5 cycles. The resulting dispersion had a typical diameter of 160–220 (Z-average, Malvern Zetasizer).

The dispersion could be used directly or lyophilized for 48 hours by optionally adding a suitable cryoprotectant. The resulting cake could be easily reconstituted to the original dispersion by addition of sterile water or saline.

EXAMPLE 24

Pharmacokinetic (PK) Data for Cyclosporine Nanoparticles (Capsorine I.V.) Following Intravenous Administration Comparison with Sandimmune I.V. (Currently Marketed Formulation by Sandoz)

Nanoparticles of cyclosporine (Capsorine I.V.) prepared as described above (Examples 22 and 23) were reconstituted in saline and administered to a first group of 3 Sprague Dawley rats by intravenous bolus. A second group of 3 rats were given Sandimmune I.V., which contains Cremaphor/Ethanol after dilution in saline. Each group received the same dose of 2.5 mg/kg. Blood samples were taken at times 0, 5, 15, 30 (minutes) 1, 2, 4, 8, 24, 36 and 48 (hours). Levels of cyclosporine in the blood were assayed by HPLC and typical PK parameters were determined. The PK curves showed typical decay over time as follows:

|  | Decay Over Time | |
| --- | --- | --- |
|  | AUC, mg-hr/ml | Cmax, ng/ml |
| Capsorine I.V. | 12,228 | 2,853 |
| Sandimmune I.V. | 7,791 | 2,606 |

In addition, due to toxicity of the Sandimmune I.V. formulation, 2 of 3 rats in that group died within 4 hours after dosing. Thus the nanoparticle formulation (Capsorine I.V.) according to the present invention shows a greater AUC and no toxicity compared to the commercially available formulation (Sandimmune I.V.).

EXAMPLE 25

Pharmacokinetic (PK) Data for Cyclosporine Nanodroplets (Capsorine Oral) Following Oral Administration Comparison with Neoral (Currently Marketed Formulation by Sandoz)

Nanodroplets of cyclosporine prepared above were administered in orange juice, to a first group of 3 Sprague Dawley rats by oral gavage. A second group of 3 rats were given Neoral, a commercially available microemulsion formulation containing emulsifiers, after dilution in orange juice, also by oral gavage. Each group received the same dose of 12 mg/kg in an identical volume of orange juice. Blood samples were taken at times 0, 5, 15, 30 (minutes) 1, 2, 4, 8, 24, 36 and 48 (hours). Levels of cyclosporine in the blood were assayed by HPLC and typical PK parameters were determined. The PK curves showed typical decay over time as follows:

|  | Decay Over Time | |
| --- | --- | --- |
|  | AUC, mg-hr/ml | Cmax, ng/ml |
| Capsorine Oral | 3,195 | 887 |
| Neoral | 3,213 | 690 |

Thus, the nanodroplet formulation (Capsorine Oral) of the present invention shows a similar PK behavior to the commercially available formulation (Neoral).

While the invention has been described in detail with reference to certain preferred embodiments thereof, it will be understood that modifications and variations are within the spirit and scope of that which is described and claimed.

That which is claimed is:

1. A method for the preparation of a substantially water insoluble pharmacologically active agent for in vivo delivery, said method comprising:
    subjecting a mixture comprising:
        an organic phase containing said pharmacologically active agent dispersed therein, and
        aqueous medium containing biocompatible polymer, wherein said mixture contains substantially no surfactants, to high shear conditions in a high pressure homogenizer at a pressure in the range of about 3,000 up to 30,000 psi.

2. A method according to claim 1 further comprising removing said organic phase from said mixture.

3. A method according to claim 1 further comprising removing said aqueous phase from said mixture.

4. A method according to claim 1 wherein said substantially water insoluble pharmacologically active agent is selected from a pharmaceutically active agent, a diagnostic agent, or an agent of nutritional value.

5. A method according to claim 4 wherein said pharmaceutically active agent is selected from the group consisting of analgesics/antipyretics, anesthetics, antiasthamatics, antibiotics, antidepressants, antidiabetics, antifungal agents, antihypertensive agents, anti-inflammatories, antineoplastics, antianxiety agents, immunosuppressive agents, antimigraine agents, sedatives/hypnotics, antianginal agents, antipsychotic agents, antimanic agents, antiarrhythmics, antiarthritic agents, antigout agents, anticoagulants, thrombolytic agents, antifibrinolytic agents, hemorheologic agents, antiplatelet agents, anticonvulsants, antiparkinson agents, antihistamines/antipruritics, agents useful for calcium regulation, antibacterial agents, antiviral agents, antimicrobials, anti-infectives, bronchodialators, hormones, hypoglycemic agents, hypolipidemic agents, proteins, nucleic acids, agents useful for erythropoiesis stimulation, antiulcer/antireflux agents, antinauseants/antiemetics, oil-soluble vitamins, as well as mitotane, visadine, halonitrosoureas, anthrocyclines and ellipticine.

6. A method according to claim 4 wherein said pharmaceutically active agent is an antineoplastic selected from adriamycin, cyclophosphamide, actinomycin, bleomycin, duanorubicin, doxorubicin, epirubicin, mitomycin, methotrexate, fluorouracil, carboplatin, carmustine (BCNU), methyl-CCNU, cisplatin, etoposide, interferon, camptothecin and derivatives thereof, phenesterine, paclitaxel and derivatives thereof, taxotere and derivatives thereof, vinblastine, vincristine, tamoxifen, etoposide or piposulfan.

7. A method according to claim 4 wherein said pharmaceutically active agent is an immunosuppressive agent selected from cyclosporine, azathioprine, mizoribine or FK506 (tacrolimus).

8. A method according to claim 4 wherein said diagnostic agent is selected from ultrasound contrast agents, radiocontrast agents, or magnetic contrast agents.

9. A method according to claim 4 wherein said agent of nutritional value is selected from amino acids, sugars, proteins, carbohydrates, fat-soluble vitamins, or fat, or combinations of any two or more thereof.

10. A method according to claim 1 wherein said organic phase has a boiling point of no greater than about 200° C.

11. A method according to claim 10 wherein said organic phase is selected from soybean oil, coconut oil, olive oil, safflower oil, cotton seed oil, sesame oil, orange oil, limonene oil, aliphatic, cycloaliphatic or aromatic hydrocarbons having 4–30 carbon atoms, aliphatic or aromatic alcohols having 2–30 carbon atoms, aliphatic or aromatic esters having 2–30 carbon atoms, alkyl, aryl, or cyclic ethers having 2–30 carbon atoms, alkyl or aryl halides having 1–30 carbon atoms, optionally having more than one halogen substituent, ketones having 3–30 carbon atoms, polyalkylene glycol, or combinations of any two or more thereof.

12. A method according to claim 10 wherein said organic phase comprises a mixture of a substantially water immiscible organic solvent and a water soluble organic solvent.

13. A method according to claim 1 wherein said biocompatible polymer is a naturally occurring polymer, a synthetic polymer, or a combination thereof.

14. A method according to claim 1 wherein said biocompatible polymer is capable of being crosslinked by disulfide bonds.

15. A method according to claim 13 wherein said naturally occurring polymers are selected from proteins, peptides, polynucleic acids, polysaccharides, proteoglycans or lipoproteins.

16. A method according to claim 13 wherein said synthetic polymers are selected from synthetic polyamino acids containing cysteine residues and/or disulfide groups; polyvinyl alcohol modified to contain free sulfhydryl groups and/or disulfide groups; polyhydroxyethyl methacrylate modified to contain free sulfhydryl groups and/or disulfide groups; polyacrylic acid modified to contain free sulfhydryl groups and/or disulfide groups; polyethyloxazoline modified to contain free sulfhydryl groups and/or disulfide groups; polyacrylamide modified to contain free sulfhydryl groups and/or disulfide groups; polyvinyl pyrrolidinone modified to contain free sulfhydryl groups and/or disulfide groups; polyalkylene glycols modified to contain free sulfhydryl groups and/or disulfide groups; polylactides, polyglycolides, polycaprolactones, or copolymers thereof, modified to contain free sulfhydryl groups and/or disulfide groups; as well as mixtures of any two or more thereof.

17. A method according to claim 1 wherein said high shear conditions comprise contacting said organic phase and said aqueous medium in a high pressure homogenizer at a pressure in the range of about 6,000 up to 25,000 psi.

18. A method according to claim 1 wherein said biocompatible polymer is the protein albumin.

19. A method according to claim 1 wherein said aqueous medium is selected from water, buffered aqueous media, saline, buffered saline, solutions of amino acids, solutions of sugars, solutions of vitamins, solutions of carbohydrates, or combinations of any two or more thereof.

20. A method according to claim 1 wherein said high shear conditions produce particles comprising said pharmacologically active agent coated with said biocompatible polymer.

21. A method according to claim 20 wherein said particles have an average diameter of less than 1 micron.

22. A method according to claim 20 wherein said particles have an average diameter of less than 200 nm.

23. A method according to claim 22 wherein said mixture is sterile filtered.

24. A method according to claim 20 wherein said particles are amorphous, crystalline, or a mixture thereof.

25. A method according to claim 24 wherein said particles are substantially amorphous.

26. A method for the preparation of a substantially water insoluble pharmacologically active agent for in vivo delivery in the form of sterile-filterable particles, said method comprising:

subjecting a mixture comprising:
an organic phase containing said pharmacologically active agent dispersed therein, wherein said organic phase comprises a mixture of a substantially water immiscible organic solvent and a water soluble organic solvent, and
aqueous medium containing biocompatible polymer,
wherein said mixture contains substantially no surfactants, to high shear conditions in a high pressure homogenizer at a pressure in the range of about 3,000 up to 30,000 psi.

27. A method according to claim 26 further comprising removing said organic phase from said mixture.

28. A method according to claim 26 further comprising filtering said mixture through a 0.22 micron filter.

29. A method according to claim 26 further comprising removing said aqueous phase from said mixture.

30. A method according to claim 26 wherein said high shear conditions produce amorphous particles, crystalline particles, or a mixture thereof.

31. A method according to claim 30 wherein said particles are substantially amorphous.

* * * * *